United States Patent [19]
Kindiger et al.

[11] Patent Number: 5,710,367
[45] Date of Patent: Jan. 20, 1998

[54] APOMICTIC MAIZE

[75] Inventors: Bryan K. Kindiger, Woodward, Okla.; Victor Sokolov, Novosibirsk, Russian Federation

[73] Assignee: The United States of America as represented by the Secretary of Agriculture, Washington, D.C.

[21] Appl. No.: 532,904

[22] Filed: Sep. 22, 1995

[51] Int. Cl.$^6$ .................. A01H 5/00; C12M 15/00
[52] U.S. Cl. .................. 800/200; 800/250; 800/DIG. 56; 47/58; 47/DIG. 1; 435/172.1; 536/24.3
[58] Field of Search ............... 800/200, 205, 800/250, DIG. 56; 435/172.3, 172.1, 412, 430, 424; 47/58, DIG. 1; 536/24.3

[56] References Cited

U.S. PATENT DOCUMENTS 5,330,547  7/1994  Eubanks ................................. 47/58

FOREIGN PATENT DOCUMENTS

WO8900810  2/1989  WIPO ........................... A01H 1/00

OTHER PUBLICATIONS

Haring et al. The use of transgenicn plants to understand transposition mechanisms and to develop transposon tagging strategies. PLant Molecualr Biology 16: 449–461, 1991.
Shaw et al. Structural features of the Maize sus 1 Gene and Protein. Plant Physiology 106:1659–1665, 1994.
Yudin, B.F. Experimental polyploidy and study of apomixis in maize, In Apomixis and Breeding, Ed. SS Khokhlov. ARS USDA, 1970.
Asker, S. E. and L. Jerling. (1992). Apomixis in Plants. 1$^{st}$ Edition. CRC Press, Boca Raton, FL., pp. 241–277.
deWet, J. M. J., L. M. Engle, C. A. Grant, and S. T. Tanaka (1972). Cytology of Maize–Tripsacum introgression. Amer. J. Bot. 59:1026–9.
deWet, J. M. J., Harlan, J. R. (1974). Tripsacum–maize Interaction: A novel cytogenetic system. Genetics 78:493–502.
Dujardin, M. and Hanna, W. W. (1983). Apomictic and sexual pearl millet x Pennisetum squamulatum hybrids. J. of Heredity 74:277–279.
Dujardin, M. and Hanna, W. W. (1989). Developing apomictic pearl millet–Characterization of a BC3 plant. J. Genet. Breed. 43:145–151.
Harlan, J. R. and J. M. J. deWett (1977). Pathways of genetic transfer from Tripsacum to Zea mays. Proc. Natl. Acad. Sci. USA 74:3494–7.

Hanna, W. W., J. B. Powell, J. C. Millot & Burton, G. W. (1973). Cytology of obligate sexual plants in Panicum maximum Jacq. and their use in controlled hybrids. Crop Sci. 13:695–697.
Kindiger, B. (1990). Cytological evidence supporting a procedure for directing and enhancing pairing between maize and Tripsacum. Genome 33:495–500.
Kindiger, B. and Dewald, C. (1994a). Genome accumulation in eastern gamagrass, Tripsacum dactyloides (L). L. (Poaceae). Genetica 92:197–201.
Kindiger, B. and Vierling, R. (1994b). Comparative isozyme polymorphisms of North American eastern gamagrass, Tripsacum dactyloides var. dactyloides and maize, Zea mays L. Genetica 94:77–83.
Petrov, D. F., N. I. Beloussva, E. S. Fokina & Sorokina, T. P. (1978). The engaging of chromosome parts of Tripsacum in the chromosome of maize as related to transmission transferring of apomixis elements. 14th International Congress of Genetics, Moscow, pp.46–75.
Petrov, D. F., N. I. Belousova and Fokina, E. S. (1979). Inheritance of apomixis and its elements in corn–Tripsacum hybrids. Genetika 15:1827–1836.
Petrov, D. F., N. I. Belousova, E. S. Fokina, L. I. Laikova, R. M. Yatsenko and Sorokina, T. P. (1984b). Transfer of some elements of apomixis from Tripsacum to maize. In D. F. Petrov (ed.) Apomixis and Its Role in Evolution and Breeding. Oxonian Press Ltd.,New Delhi, pp. 9–73.
Stalker, H. T., J. R. Harlan, J. M. J. deWet (1978). Genetics of Maize–Tripsacum introgression. Caryologia 31:271–282.
Wilson, K. J. and R. A. Jefferson. (1992). Preface. In K. J. Wilson (ed.) Proceedings of the International Workshop on Apomixis in Rice, Changsha, People's Republic of China. 13 Jan.–15 Jan. 1992. Hunan Hybrid Rice Research Center, Changsha, People's Republic of China.
Yudin, B. F. and Sokolov, V. A. (1989). Towards regular apomixis in maize, achieved by experiment. Genetic Manipulation in Plants 5:36–40.

Primary Examiner—Gary Benzion
Attorney, Agent, or Firm—M. Howard Silverstein; Curtis P. Ribando; John D. Fado

[57] ABSTRACT

Apomictic maize/Tripsacum hybrids having a ratio of maize chromosomes: Tripsacum chromosomes of at least 30:9 have been developed. These hybrids are useful for introgressing diplosporous apomictic reproduction into a maize background toward the ultimate goal of establishing immortalized commercial lines of apomictic maize having stably inherited characteristics without the need for continuously producing hybrid seed by repeated crossings of selected parental lines.

DNA primers for use in assaying maize/Tripsacum hybrids for apomictic reproduction behavior are provided.

28 Claims, 4 Drawing Sheets

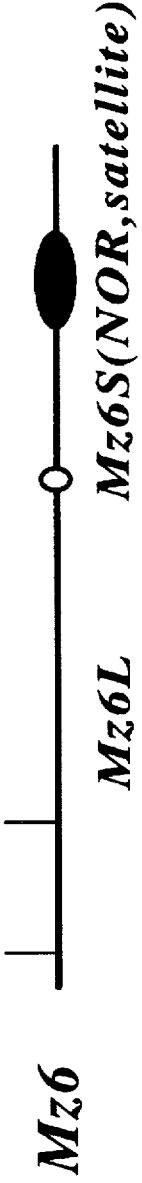
FIG. 3A-1  
FIG. 3B-1  
FIG. 3C-1
Tr16: Tr16L(NOR,satellite) Tr16S — OPA-01,OPA-06,OPA-12, OPG-06,OPI-11,OPJ-14, OPK-06 / OPC-11,OPD-08,OPF-10, OPG-03,OPG-14,OPG-18, OPJ-01
Mz6: Mz6L   Mz6S(NOR,satellite) — CSU68, UMC28, UMC134  UMC62
V9:Mz6L-Tr16L Translocation — CSU68, UMC28, UMC134  UMC62 / OPA-01,OPA-06,OPA-12, OPG-06,OPI-11,OPJ-14, OPK-06

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

CAGGCCCTTC                                                                                          10

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

GGTCCCTGAC                                                                                          10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

TCGGCGATAG                                                                                          10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:4:

GTGCCTAACC                                                                                          10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:5:

ACATGCCGTC                                                                                          10

( 2 ) INFORMATION FOR SEQ ID NO:6:

( i ) SEQUENCE CHARACTERISTICS:
        ( A ) LENGTH: 10 base pairs

-continued (B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:6:

CACCCGGATC                                                                    10

(2) INFORMATION FOR SEQ ID NO:7:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:7:

CACCTTTCCC                                                                    10

APOMICTIC MAIZE

BACKGROUND OF THE INVENTION

1. Field of the Invention

This invention relates to plants that breed true by transferring the apomictic mechanism of reproduction from a wild plant species to a cultivated plant to form a true-breeding hybrid. More particularly, this invention relates to apomictic maize and to apomictic maize/*Tripsacum* hybrids. The invention also relates to genetic elements for controlling apomixis, to vectors containing the genetic elements for controlling apomixis, to a method for using those genetic elements for producing true breeding plant progeny, and to nucleic acid sequences useful for identifying the genetic elements associated with apomixis.

Reproduction in plants is ordinarily classified as sexual or asexual. The term apomixis is generally accepted as the replacement of sexual reproduction by various forms of asexual reproduction (Rieger et al., 1976). Apomixis is a genetically controlled method of reproduction in plants where the embryo is formed without union of an egg and a sperm nuclei. There are three basic types of apomictic reproduction: 1) apospory—embryo develops from a chromosomally unreduced egg in an embryo sac derived from the nucellus, 2) diplospory—embryo develops from an egg in an embryo sac derived from the unreduced megaspore mother cell, and 3) adventitious embryony—embryo develops directly from a somatic cell. In most forms of apomixis, pseudogamy or fertilization of the polar nuclei to produce endosperm is necessary for seed viability. Obligate apomicts are believed to have a completely closed recombination system; that is, recombination occurs only during microsporogenesis and is absent during megasporogenesis. In facultative apomicts, both apomictic and sexual modes of reproduction coexist.

The aforementioned types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. In addition, apomixis can increase the reproductive capacity of plants with distorted or adverse chromosome constitutions.

Apomixis can make hybrid development more efficient by eliminating the need for multiple crosses. It also simplifies hybrid production and increases genetic diversity in plant species with good male sterility systems. It would be ideal to find genes controlling obligate or a high level of apomixis in the cultivated species and be able to readily hybridize cross-compatible sexual x apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Apomictic reproduction is well represented in the polyploid grasses (Harlan et al., 1964; Connor, 1979; Bashaw et al., 1990a; Asker et al., 1992; Koltunow, 1993;) and eastern gamagrass (*Tripsacum dactyloides* (L.) L.) is no exception. Eastern gamagrass, a distant relative of maize (*Zea mays* L.), is a perennial bunchgrass with both sexual and asexual reproductive forms. At the diploid level (2n=2x=36), sexual reproduction is exclusively observed, while at the triploid (2n=3x=54) and tetraploid (2n=4x=72) levels, diplosporous apomictic reproduction is the rule (Brown et al., 1958; Burson et al., 1990; Sherman et al., 1991). The mechanism of embryo sac development in apomictic *Tripsacum dactyloides* is characterized as being diplosporic pseudogamy of the *Antennaria* type (Brown et al., 1958; Burson et al., 1990; Leblanc et al., 1995). In this system, double fertilization of both the polar nuclei and egg does not occur. Fertilization of the polar nuclei stimulates apomictic development of the unreduced egg cell.

Wheat, rice, sorghum and maize are among the major crop species which provide much of the world's food resources. It has been suggested that the development of apomictically reproducing forms of such graminaceous crops would provide a major contribution toward food security in developing nations (Wilson et al., 1992). Of particular interest in the agricultural community is achieving an effective level of apomictic reproduction in hybrid maize. Accomplishing that goal could provide a dramatic change in the use and production of this cereal grain in the maize-growing regions of the world by providing an infinite succession of generations which would perpetuate the original level of hybrid vigor, disease resistance and additional genetic attributes apportioned in a F1 hybrid.

2. Description of the Prior Art

*Tripsacum* was first hybridized with maize by Mangelsdorf et al. (1931). Additional studies demonstrated the possibilities for generating fertile hybrids between the two species (Mangelsdorf et al., 1939; Galinat, 1973). Studies conducted by other researchers further suggest the potential for introgressing *Tripsacum* germplasm into maize (Maguire, 1961, 1962; Reeves et al., 1964; deWet et al., 1972; Simone et al., 1976; Bergquist, 1981; Cohen et al., 1984). Petrov and colleagues addressed the possibility of transferring the genes controlling apomixis from *Tripsacum* to maize for the development of true-breeding hybrids (Petrov, 1957; Petrov et al., 1984a) and reported successful results (Petrov et al., 1984b); unfortunately, genetic studies on these materials (Yudin et al., 1989) refute those findings.

During a classic maize/*Tripsacum*//maize backcrossing scheme, once the 56 chromosome (20 maize+36 *Tripsacum*) or 38 chromosome (20 maize+18 *Tripsacum*) level is achieved, there usually occurs either a partial or complete loss in apomictic reproduction (deWet et al., 1974). Materials retaining even a partial expression of apomictic reproduction at or beyond this level would be useful for further study and likely candidates for attempting introgression of apomixis to maize.

Intercrossing sexually reproducing individuals with apomictic individuals has been successfully utilized to elucidate the mechanism of apomixis in several species within the Gramineae. Harlan et al., (1964) utilizing both embryological and crossing studies of sexual x sexual, sexual x apomictic, and apomictic x sexual accessions of *Bothriochloa* and *Dichanthium*, proposed a two locus system to explain the inheritance of apomixis in these species. Apomicts were assumed to be heterozygous for the apomictic genes, and apomixis was dominant to sexuality. Sexual diploids were suspected to be of the a1 a1 a2 a2 genotype while apomictic tetraploids were of the A1 A1 a1 a1 A2 A2 a2 a2 genotype. In addition, a balanced genotypic relationship between the two loci was indicated.

In *Paspalum*, Burton et al. (1960) investigated the genetic control of apomixis by generating sexual tetraploids. In this scheme, a sexual tetraploid was crossed to an obligate apomictic tetraploid with subsequent generation of a sexual autotetraploids. Analysis of this data indicated that apomixis was conditioned by a few recessive genes.

Hanna et al., (1973), by intercrossing naturally occurring sexual tetraploids with naturally occurring tetraploid apomictics of *Panicum maximum* and evaluating the progeny, proposed that apomictic reproduction in this species was recessive to sexuality and that the method of reproduction was probably controlled by at least two loci.

Studies utilizing sexual and apomictic maize/*Tripsacum* hybrids have predicted a heterozygous two gene system (Petrov et al., 1978, 1979). One set of genes controls non-reduction of the egg (N) while the other set controls apomictic (parthenogenic) development of that egg (A). The proposed genetic constitution of an apomictic tetraploid *Tripsacum* is N N n n A A a a. Based on the segregations observed among apomictic 56-chromosome (20 maize+36 *Tripsacum*) and apomictic, 38 chromosome (20 maize+18 *Tripsacum*) maize-*Tripsacum* backcross hybrids, the two sets of genes are presumed to be linked (Petrov et al., 1978, 1979). The genetic constitution of a sexual diploid was not proposed. Recent investigations by Kindiger and Dewald (unpublished) performed on a set of *T. dactyloides* triploids, segregating for sexual and apomictic reproductive systems, also suggest that apomixis is controlled by two dominant genes.

Notwithstanding the motivation for introducing the apomictic trait into normally sexual crops and certain success in hybridizing cultivated species with distantly related wild species having genes controlling apomixis, introgression of apomixis into sexual crops has not heretofore been achieved. In many cases, attempts were thwarted by unavailability of related apomictic wild types or in failure of accomplishing direct hybridization between cultivated varieties and the wild type. Asker (1992) reports that attempts to introduce the apomictic trait into wheat, barley, sorghum, sugar beets, maize, and a variety of other crops have largely been unsuccessful.

To date, the most successful project directed toward apomixis is the transfer of gene(s) controlling apomixis from wild to cultivated species of *Pennisetum* (Dujardin, 1983, Dujardin et al., 1989). Interspecific hybrids with pearl millet generally have been highly male sterile. However, normal male meiosis in an apomictic hybrid, resulting in fertile pollen, is usually a prerequisite for continued crossing since an inherent property of apomixis is the lack of meiotically reduced (i.e. recombinant) female gametes. Progress with introgressing the apomictic gene(s) in pearl millet has been achieved by elevating male fertility in complex hybrids produced between induced tetraploid pearl millet (2n=4x=28), the wild apomictic species, *P. squamulatum* Fresen (2n=6x=54) and a third species, *P. purpureum* Schum. (2n=4x=28), (Dujardin et al., 1989, herein incorporated by reference). Maxon et al. (1989) have also reported some progress in the transfer of an apomixis-like phenomenon to a sexual species (soybean) by treating plants with asexually transmissible male sterility factors (AMS vectors).

SUMMARY OF THE INVENTION

We have now succeeded in demonstrating that an apomictic mechanism can be transferred from a wild species to a predominantly cultivated species background in order to provide a true-breeding plant characterized by apomictic development. Specifically, we have generated apomictic maize/*Tripsacum* hybrids having a higher proportion of maize chromosomes than heretofore reported in the prior art. Within the scope of the invention are hybrids having a ratio of maize chromosomes:*Tripsacum* chromosomes of at least 30:9. Karyotypes comprising from 30–70 chromosomes of maize and 9 chromosomes of *Tripsacum* are illustrated including one in which the long arm of *Tripsacum* chromosome 16 carrying the genes for apomixis is translocated to the long arm of maize chromosome 6. A representative hybrid having 30 chromosomes of *Zea mays* and 9 chromosomes of *Tripsacum dactyloides* has been deposited in the ATCC depository.

In accordance with the object of the invention to introgress apomictic reproduction into a plant which normally propagates itself by sexual reproduction, we have successfully produced maize/*Tripsacum* hybrids which are more genotypically maize-like than hybrids heretofore known in the prior art. These hybrids contain dominant genetic material which provides for the omission of sexual reproductive processes and their replacement by an apomictic form of reproduction, commonly referred to as diplosporous apomixis of the *Antennaria* type.

It is also an object of the invention to provide maize plants which possess a specific set of 9 chromosomes from *Tripsacum* and 30–70 chromosomes of maize, which possess the capacity for diplosporous apomictic reproduction. These plants are useful as breeding stock for producing apomictic hybrids having an even greater complement of maize chromosomes and reduction in the number of *Tripsacum* chromosomes.

Another object of the invention is to provide a basis for establishing immortalized commercial lines of obligate apomictic maize having stably inherited characteristics without the need for continuously producing hybrid seed by multiple or repeated crossings with selected parental lines.

Still another object of the invention is to provide a series of DNA markers for use in assaying maize/*Tripsacum* hybrids for apomictic reproduction behavior.

It is also an object of the present invention to provide genes governing and controlling diplosporous apomictic reproduction, as well as the assignment of the genes to a particular molecular linkage group based upon their association with molecular markers and location of the genes to a specific chromosome based upon cytogenetic and molecular investigation.

Finally, it is an object of this invention to provide genetic material which can be manipulated by classical plant breeding methods, cell and tissue culture methods, and/or plant transformation and genetic engineering techniques to introduce the desired genes into maize as well as additional plant species which can then be clonally selected, regenerated and propagated to produce individuals capable of diplosporous apomictic reproduction.

Other objects and advantages of this invention will become readily apparent from the ensuing description.

Deposit of Seeds

A sample comprising at least 2500 seeds of the hybrid comprising 30 chromosomes of *Zea mays* and 9 chromosomes of *Tripsacum dactyloides*, representing the family referred to herein as V162 was deposited on Jul. 27, 1995, under the conditions of the Budapest Treaty with the American Type Culture Collection, 12301 Parklawn Drive, Rockville, Md. 20852, and has been assigned Accession Number ATCC 97233.

BRIEF DESCRIPTION OF THE DRAWINGS

FIG. 3. presents a comparison of *Tripsacum* chromosome 16

FIGS. 3A and 3A-1 maize chromosome 6

FIGS. 3C and 3C-1 and the Mz6L-Tr16L translocation

FIGS. 3A, 3B, and 3C present together with associated RAPD primers and RFLP markers.

Figure 1:
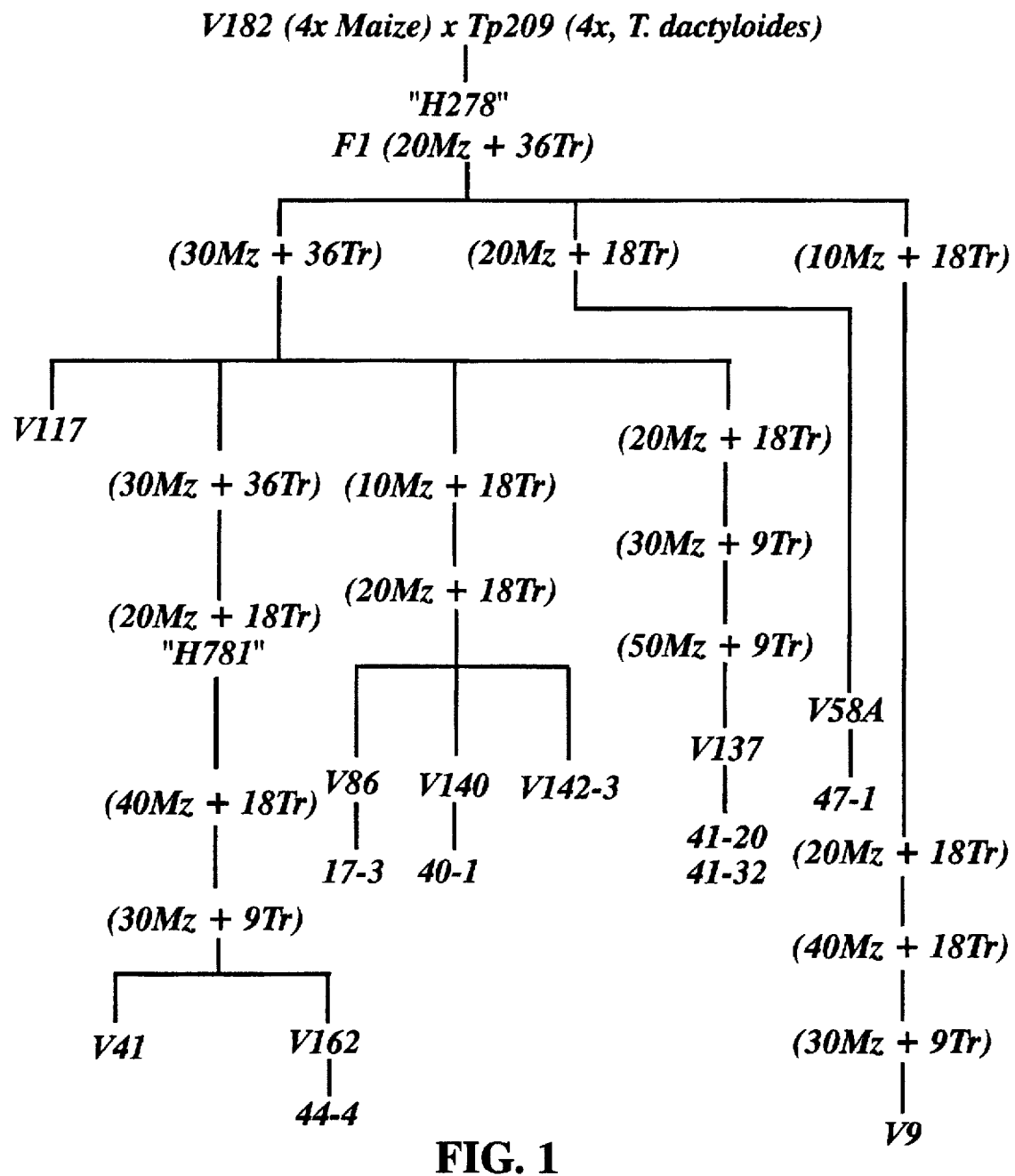
FIG. 1 shows the general pedigree/relationship among the five families used to develop RAPD markers associated with apomictic reproduction.

Glossary apomixis: replacement of sexual reproduction by various forms of asexual reproduction. Obligate apomicts are believed to have a completely closed recombination system while in facultative apomicts, apomictic and sexual modes of reproduction coexist.

$B_{III}$ hybrid: an individual generated from the fusion of an unreduced egg (2n) with a reduced sperm nuclei (n).

diplosporic pseudogamy: fertilization of the polar nuclei by sperm whereby apomictic development of the unreduced egg cell is stimulated.

linkage group: the sequential arrangement of genes or molecular markers positioned on any one chromosome.

meiosis: a type of nuclear division associated with sexual reproduction, producing four haploid cells from a single diploid cell, the process involving two cycles of division. Meiosis serves to halve the number of chromosomes to prevent a doubling in each generation and to produce a mixing of genetic material in the daughter cells by independent assortment and recombination.

Mz6L-Tr16L-satellite (or Mz6L-Tr16L) chromosome: maize Chromosome No. 6 having translocated to the distal end of its long arm the long arm of *Tripsacum* Chromosome No. 16 (Tr16).

polyembrony: the development of several embryos within a single ovule; the case where a zygote gives rise to more than one embryo, as in identical twins.

RAPD: random amplified polymorphic DNA.

RFLP: random fragment length polymorphisms

DETAILED DESCRIPTION OF THE INVENTION

GENETIC MODEL

As a basis for understanding the mechanism for introgressing apomixis from *Tripsacum dactyloides* into maize, we have developed a genetic model for the inheritance and segregation of apomictic elements in *Tripsacum*. While not desiring to be bound to any particular theory, this model is presented here as context for understanding the ensuing description of the invention. The proposed genetic model and its genotypic combinations for apomictic inheritance in *T. dactyloides* are provided in Table I, below.

TABLE I

Model for Inheritance and Segregation of Apomictic Elements in Triploid *Tripsacum dactyloides* Hybrids Generated from a Sexual Diploid × Apomictic Tetraploid Cross

| Genetic Constitution* | Expected Frequency | | Maternal Fertility | Mode of Reproduction |
|---|---|---|---|---|
| N N n A A a | 1 | } 3 | high fertility triploid | apomictic |
| N n n A A a | 2 | | intermediate fertile triploid | apomictic |
| n n n A A a | 1 | } 13 | sterile | sexual |
| N N n A a a | 2 | | near complete sterility, >99% | sexual |
| N n n A a a | 4 | | near complete sterility, >99% | sexual |
| n n n A a a | 2 | | sterile | sexual |
| N N n a a a | 1 | | sterile | sexual |
| N n n a a a | 2 | | sterile | sexual |
| n n n a a a | 1 | | sterile | sexual |

*The triploids are generated by crossing a sexual diploid (n n a a) with an apomictic tetraploid (N N n n A A a a).

The model consists of two independently segregating loci with the following assumptions: (I) N is the dominant allele for non-reduction; (II) A is the dominant allele for apomictic development of an unreduced egg (parthenogenesis); (III) the genes for non-reduction (N) and apomixis (A) are epistatic and incompletely dominant and subsequently required in two doses for predictable non-reduction and apomictic development of the egg to occur. One dose of N with two doses of A may produce a "leaky" phenotype where non-reduction and possible apomictic development are occasional, but not frequent (rarely exceeds 40% fertility); (IV) a proper dosage or balance of the two gene sets (N, n and A, a) is a necessary component for frequent apomictic development; (V) two classes of "fertile" triploids exist, and each maintains a slightly different genetic constitution (N N n A A a=highly fertile triploids and N n n A A a=intermediate fertile triploids); and (VI) all additional genotypic segregation products are sexual (non-apomictic) in their development (undergo meiosis) and are considered highly sterile due to their triploid condition. This is not to imply, however, that extremely low levels of apomictic development, expressed as female fertility, may rarely occur in some individuals within this class (i.e., N N n A a a and N n n A a a).

Based on the expectations shown in Table I and the parameters outlined above, a ratio of 13 steriles: 2 intermediate fertiles: 1 highly fertile is expected. Highly fertile individuals should carry the N N n A A a genotype. Individuals of intermediate fertility will carry the N n n A A a genotype. Sterile or nearly complete sterile individuals will carry all other genotypic combinations.

This model was confirmed in a study of 387 triploid (2n=3x=54) hybrids of *T. dactyloides* produced by crossing sexual diploid (2n=36) individuals with apomictic tetraploid (2n=4x=72) pollen parents. Likewise, 90 triploid progeny resulting from a cross between a sexual diploid and a "synthetic" or $B_{III}$-derived apomictic tetraploid also segregated in the proposed 13:2:1 ratio. In addition, $B_{III}$-derived tetraploid hybrids generated from sterile triploids (2n+n matings) are occasionally generated. The model predicts that such 4x $B_{III}$ hybrids will be sterile and non-apomictic. This was confirmed in crosses of four highly sterile 3x hybrids which generated four $B_{III}$ derived tetrapoloids. Each of the $B_{III}$-derived tetraploids were highly sterile (exceeding 99%).

Lastly, cytogenetic and molecular evaluations on the sexual and apomictic maize-Tripsacum hybrids and apomictic maize 6L-Tr16L translocation stock indicated only one chromosome arm carries the genes conferring apomictic reproduction. This indicates that the alleles N and A are located on Tr16L.

GENERATION OF 39 CHROMOSOME APOMICTIC MAIZE/TRIPSACUM HYBRIDS

Preceeding the work of this invention, a maize/*Tripsacum dactyloides* hybrid, hereafter referred to as H278, was developed in Russia by Petrov et al. (1984b). This hybrid, possesses a karyotype of 20 maize and 36 *Tripsacum* chromosomes and was used to generate several 56 chromosome (20 maize+36 *Tripsacum* chromosome) apomictic hybrids genetically identical to H278 by backcrossing with maize. Subsequent backcrosses to H278 utilizing a local openpollinated, diploid maize cultivar (Petrov et al., 1984b) resulted in the generation of five individuals with 38 chromosomes (20 maize+18 *Tripsacum*). Of these, 3 individuals were observed to generate progeny which were derived by meiotic or sexual reproductive behaviors. The fourth individual was completely sterile while a fifth individual produced progeny with a chromosome count of 38 (H781). Following 15 generations of continuous backcrossing with both diploid (2n=2x=20) and tetraploid (2n=4x=40) maize testers, a large number of individuals and families possessing 10–30 maize chromosomes and 18–36 *Tripsacum* chromosomes were eventually generated from this single individual (H781). Recent studies of materials derived from H781 have confirmed their ability to reproduce by apomixis (Kindiger et al., 1995a).

The apomictic materials of this invention were derived from the aforementioned 38 chromosome apomictic (20mz+ 18 Tr) hybrid by additional backcrosses with both diploid and tetraploid maize testers and screening for a 58 chromosome backcross hybrid (40Mz+18Tr). This 58-chromosome individual is the product of a genome accumulation event whereby an unreduced egg does not develop apomictically, but remains receptive to fertilization by a sperm nuclei to form a $B_{III}$ hybrid (i.e. a 2n+n mating). The identified 58 chromosome hybrid was backcrossed by a diploid maize tester. Seed generated from the cross gave rise to individuals with 30 maize+9 *Tripsacum* chromosomes as shown in the left-most branch of the pedigree tree in FIG. 1. The 39 chromosome progeny are the result of a complete sexual event, whereby a reduced egg cell possessing 20Mz+9Tr chromosomes was fertilized by a haploid (n=10) sperm nuclei. This resulted in the generation of a 30Mz+9Tr chromosome individual.

In the hybrids described herein, there is evidence of partial male fertility, a useful trait for enabling fertilization of the polar nuclei and consequent production of viable seed. However, pollen necessary for endosperm and seed development can be furnished by any maize pollen source, or 'nurse' cultivar in a commercial breeding program and would be grown in the proximity of the apomictic hybrid to enable pollination to take place. The pollen source would not, of course, affect the genetics of the apomictic cultivar since the unreduced egg of the cultivar develops by parthenogenesis. Several families of apomictic maize/*Tripsacum* hybrids have been produced by the aforementioned procedure. In each case, the same 9 *Tripsacum* chromosomes are present; namely, *Tripsacum* chromosomes 7, 10, 11, 12, 13, 14, 16, 17, and 18. This set of chromosomes has been designated as set 9B. Cytological examination reveals that these 9 chromosomes are generally the smaller of the 18 normally present in *Tripsacum*. They can be positively identified by cytological observation or in RAPD assays using specific primers (e.g. decamer primers) as described in more detail in Example 2, below.

Based on results of a RAPD study involving sexual and apomictic individuals derived from plants having either 18 or 9 *Tripsacum* chromosomes, we have determined that among the sexual backcross hybrids, 8 of 9 linkage groups are represented. This leaves only one linkage group available for carrying the genes for apomixis. Therefore, it is concluded that the genes, A and N, reside on one chromosome and are spatially distributed at a sufficient distance in that they can segregate independently following recombination during pollen/microspore development. Accordingly, these genes are characterized as being unlinked.

Assignment of the apomictic genes to the long arm of Tr16 (Tr16L) was made by studying specific maize/*Tripsacum* hybrids. In karyotyping a non-apomictic (sexual) maize-*Tripsacum* hybrid (V142-3) with 40 maize and 8 *Tripsacum* chromosomes from the 9B set, it was observed that Tr16 was absent in the *Tripsacum* chromosome set indicating that it must be associated with apomixis. Secondly, in a root tip squash of an apomictic individual (V9) with a Mz6L-Tr16L-satellite chromosome (translocated Tr16L, see discussion below), it was observed that the plant was missing the short arm of Tr16 but possessed the Tr16L segment translocated to the distal tip of Mz6L (see Example 4). Therefore, by inference, the genes for apomixis must reside on the long arm of Tr16 (satellite end).

One family of 39-chromosome apomictic maize/*Tripsacum* hybrids designated as V9 was derived from the original F1 hybrid, H278, as shown in FIG. 1. It is similar to the derivation of V162 but is a product of a reduction division generating an individual with 10Mz+18Tr chromosomes. The V9 individuals are unique in that they are characterized by a Mz6L-Tr16L translocation resulting from a partial meiotic event allowing pairing between homoeologous regions of Mz6 and Tr16. This translocation is different from, but analogous to, the translocation at maize chromosome 9 described by Maguire (1961, 1962) and Kindiger et al. (1990). Identification of the maize and *Tripsacum* chromosomes involved in the Mz6L-Tr16L translocation was facilitated due to each chromosome carrying a nucleolus organizing region (NOR) and a satellite. The classic karyotype of maize shows the maize satellite residing on 6S, while a karyotype of *Tripsacum* shows the satellite to be located on 16L. The Mz6L-Tr16L translocation possesses a satellite at both ends of chromosome 6 with a small addition of the Tr16L segment. See FIG. 3 and further discussion in Examples 2 and 3, below.

CHARACTERISTICS OF APOMICTS

The aspects of apomictic reproduction in hybrids of this invention are characterized as follows:

Apomictic Progeny

Apomictic progeny can be identified by a plurality of techniques. Most progeny possess the same chromosome count as their apomictic parents, except in the case of $B_{III}$ hybrids. Thus, for example, the progeny of 39 chromosome individuals would also possess 39 chromosomes, or in the case of $B_{III}$-hybrids, 49 or 59 chromosomes. Standard cytological methods as known in the art can be used for determining the number of chromosomes in an individual. Genetic uniformity would expectedly occur among progeny and between progeny and parent. Such uniformity can be ascertained, for example, by progeny testing, isozyme and molecular methods. Occasionally, however, variation is observed in molecular banding profiles between related apomicts as the result of the occurrence of $B_{III}$ hybrids, as discussed in further detail, below.

$B_{III}$ Hybrids

A $B_{III}$ hybrid is defined as an individual generated from the fusion of an unreduced egg (2n) with a reduced sperm nuclei (n). Such 2n+n matings have been well-documented in Cenchrus (Bashaw et al., 1990b), Paspalum (Burson, 1992), Pennisetum (Bashaw et al., 1992) and more recently in Tripsacum (Kindiger et al., 1994a). As a unique reproductive feature of apomictic development in T. dactyloides, it was expected that such behavior would be exhibited in the maize-Tripsacum hybrids if the apomictic Tripsacum genes are fully functional in a maize background. Generation of $B_{III}$ hybrids is often a relatively low frequency event. As shown in Example 2, below, the percentage of 2n+n matings arising from 39-chromosome apomicts is typically less than about 10%. The production of $B_{III}$ hybrids has not been observed in diploid forms of Tripsacum and would not be expected since these plants are sexual in their reproductive form.

Polyembryony

The occurrence of polyembryony in Tripsacum dactyloides has been observed and documented by Farquharson (1955). Polyembryony is not observed in the sexual diploid forms but is a unique feature only in the apomictic forms of Tripsacum. While not well studied, it is speculated that multiple embryos in Tripsacum arise following fertilization of the polar nuclei and apomictic stimulation of the unreduced egg cell (Farquharson, 1955). Following apomictic development of the unreduced egg, an adjacent synergid cell(s) is stimulated to spontaneously develop into a viable embryo.

In both Tripsacum and the maize-Tripsacum hybrids, twins either possess identical chromosome numbers (both apomicts) or differing chromosome numbers (one being an apomictic and the other being a $B_{III}$ derived hybrid or both being $B_{III}$ hybrids, resulting from a 2n+n hybridization). The occurrence of both twin and triplet multiple embryos has been observed in Tripsacum and in the 30Mz+9Tr apomictic hybrid materials.

The occurrence of polyembryony in maize, is however, not without precedent. Kermicle (1969) observed polyembryony in maize stocks with the ig (indeterminate gametophyte) allele which allows for the generation of androgenic haploids in maize. Lin (personal communication) and Kindiger et al. (1993) further demonstrated that polyembryony could be selectively reduced or enhanced during the development of additional ig stocks. In both cases, apomictic reproduction of these materials is not observed or expected. In the case of ig, polyembryony is associated with non-apomict lines of maize. It is, however, expected that the polyembryonic behaviors observed in the apomictic maize-Tripsacum backcross hybrids, are a true representation of the resultant successful transfer of apomictic genes from Tripsacum to such hybrids since ig was not introduced into the maize-Tripsacum hybrid materials.

Incomplete Meiosis

Polyploid Tripsacum is regarded an a facultative or near obligate apomict. As such, it has some level of sexual development (i.e. meiosis followed by fertilization of sperm and egg). It has been suggested that in some plants exhibiting mitotic diplospory, entry into meiosis occasionally occurs, but is terminated at a very early stage. It is possible that such an incomplete meiotic event would allow for genetic change with no alteration in chromosome number. This behavior is commonly referred to as a first division restitution and has been indicated in apomictic Tripsacum (Kindiger et al., 1995b). It would allow for the generation of new recombinant types without a reduction in chromosome number or infusion of new alleles from an outside pollen source. The occasional occurrence of an incomplete meiotic event also occurs in the apomictic, maize-Tripsacum hybrids. This behavior provides additional evidence for the successful transfer of apomictic elements from Tripsacum to maize and the expression of that trait in a maize background.

Ploidy Related Apomictic Expression

In Tripsacum, it has been observed that $B_{III}$ derived pentaploid (2n=5x=90) and hexaploid (2n=6x=108) hybrids generated from 2n+n matings exhibit complete or near-complete female sterility. Since, there is no opportunity for loss of the maternal genome and the apomictic gene(s) from a 2n+n mating, the contribution of an additional genome by the pollen parent must upset a balance in the gene(s) controlling apomixis. This behavior is apparently not uncommon in apomictic species (Asker and Jerling, 1992).

Observations made on the seed setting ability of maize-Tripsacum $B_{III}$ derived hybrids generated from 2n+n matings which generated apomictic 38, 48, 58 and 68 chromosome $B_{III}$-derived hybrids also indicates a tendency to lose the capacity to produce seed. Seed set varies from about 30% for individuals possessing 38 chromosomes (20 Mz+18 Tr) to about 5% for individuals possessing 58 chromosomes (40 Mz+18 Tr). Above 58 chromosomes, fertility is essentially nil.

Nucleotide Markers

As might be expected, there are unique nucleotide sequences or markers, which are associated with apomixis. Included are markers unique to the A and N alleles responsible for apomixis that can be identified by any of a variety of assays. Example 2, below, describes the use of RAPD analysis to differentiate apomictic from non-apomictic individuals.

FURTHER INTROGRESSION OF APOMIXIS INTO MAIZE BACKGROUND

A variety of techniques are envisioned for further introgressing apomictic reproduction into a maize background using any of the herein described 30Mz+9Tr hybrids as starting material. Of course, it is believed that the preferred source material for reduction of the Tripsacum chromosomal complement would be that having the Mz6L-Tr16L translocation (e.g. individuals from the V9 family).

Classical Breeding

This procedure, relies upon the strategy previously described for obtaining the 39 chromosome (30Mz+9Tr) material from the original F1 hybrid, H278. The 30Mz+9Tr materials can likewise be successively backcrossed to maize. Following a 2n+n mating, $B_{III}$-derived hybrids are selected which are apomictic and have an increase in the maize chromosome complement (i.e. genome accumulation). By following this strategy, it is possible to derive individuals with 49 (40Mz+9Tr), 59 (50Mz+9Tr), 69 (60 Mz+9Tr) and 79 (70 Mz+9Tr) chromosomes. Due to the increase in the maize genome, further reductions in the Tripsacum genetic complement are possible. Typically, the presence or accumulation of 40-70 maize chromosomes results in the occurrence of infrequent sexual events which give rise to a further, random loss of chromosomes in the Tripsacum 9B set. In this manner, plants possessing a full set of maize and a reduced set of Tripsacum chromosomes can be generated.

Due to the lack of linkage between the N and A genes, it is envisioned that a system for the development of apomictic maize F1 hybrids will be possible. Independent transfer of each gene into two complementary inbred lines of maize would result in apomictic reproduction in the hybrid. This system would be similar to the cytoplasmic male sterility/ restorer systems used in the commerical production of hybrid seed corn and sorghum.

Microspore Culture

In apomictic *Tripsacum* and the apomictic maize-*Tripsacum* hybrids, the classic behavior exhibited in diplosporous apomictics of the Antennaria type, dictates that meiosis during megasporogenesis (development of the egg) is omitted. However, meiosis during microsporogenesis (pollen development) proceeds normally. Androgenesis is the formation of an embryo whose genomic constitution is derived solely from the male gametophyte. The production of haploid plants by androgenesis has been explored in a method referred to as anther culture (Collins, 1977; Morrison et al., 1988). Established microspore methods of maize have been able to generate haploid (1n=1x=10) individuals from the reduced microspores generated from diploid (2n=2x=20) maize individuals (Ting et al., 1985; Pescitelli et al., 1988). Observations of microsporogenesis in maize-*Tripsacum* hybrids (Kindiger, 1993) has shown that meiosis is normal and that a breakdown of pollen development occurs at points following meiotic development.

Generally, classic microspore techniques utilize two media systems. The first being a Murashige and Skoog MS initiation medium for callus development (Green et al., 1975; and Conger et al., 1987), both herein incorporated by reference). Once calli are established, the culture is transferred to a regeneration media to stimulate shoot and root initiation. Developing plantlets are transferred to sterile soil mixtures for maintenance and continued development. Microspore culture methods typically isolate viable microspores prior to and at the single nucleate stage following meiosis and (prior to the mitotic divisions). There is a high likelihood for success that culturing microspores obtained from the 30Mz+9Tr and 40Mz+9Tr individuals will produce viable "haploid" microspores with a reduced Tr chromosome complement. In the case of 39 chromosome plants, diploid maize (2n=2x=20) with varying numbers of Tr chromosomes less than 5 will be one result. In addition, several aneuploid individuals with varying maize chromosome and *Tripsacum* chromosome complements will be generated. One example could be individuals with 18Mz and 0-5 Tr chromosomes. Perhaps of more value are microspores cultured from individuals with 40Mz+9Tr chromosomes. Normal meiotic segregation during microsporogenesis will provide "diploid" microspores with 20 maize chromosomes and a random sample of 0-5 Tr chromosomes. Starting with either karyotype, the goal is to generate a reduction in both the maize and *Tripsacum* chromosome complement by microspore methods and to screen the reduced products for an apomictic mode of reproduction. It is very likely that in each case, apomictic individuals possessing a karyotype consisting of the 20Mz chromosomes and Tr16 will be generated. It is necessary for the products of the microspore culture method to possess the Tr16 chromosome or a portion of it in the translocated form as in the Mz6L-Tr16L chromosome previously described. Standard methods described herein can be used to identify the presence or absence of the intact Tr16 or the Mz6L-Tr16L chromosomes in these materials.

IDENTIFYING THE GENES FOR APOMIXIS

Isolation and Cloning of a Gene via Chromosome Walking

Presently, several methods exist for identifying, characterizing and isolating a gene from a plant genome. Each rely on the use of molecular markers and their association or linkage to the gene of interest. Markers close to the gene are considered tightly linked to the gene and are of most value. Other markers associated with the gene, but not necessarily tightly linked to it, are also of use but of less immediate value. The 7 RAPD markers described in Example 2 (Section V) range in size from 200–1200 bp and are associated with apomictic development (i.e. the genes for apomixis). These markers confirm the cytological determination that Tr16 carries the genes for apomixis and provide essential evidence that the genes reside on the long arm of Tr16. These markers also provide an ideal system for following the apomictic trait and for marking the position of the genes on either arm of Tr16 or the Mz6L-Tr16L translocation.

The bands generated in a RAPD assay can be isolated from the agarose gel and cloned in *E. Coli* type plasmids (vectors). The clones can be used as RFLP markers for identifying the presence or absence of apomixis in any *Tripsacum* species or maize-*Tripsacum* hybrid.

In addition, the 7 RAPD markers are associated with particular regions of DNA located on the Tr16 chromosome. The spatial distribution of the markers along the Tr16 chromosome can be employed in locating the A and N genes controlling apomictic reproduction. The order, position and spatial relationship between the markers and genes can thereby be mapped by conventional methods in the art. Once the positions of the genes are identified, standard gene isolation techniques can be used. For instance, the chromosomes can be isolated via methods such as pulse gel electrophoresis or standard agarose electrophoresis utilizing the markers as base or foundation points for extraction. Once the desired region is isolated, it can be sequenced by standard methods known in the art.

Isolation and Cloning of a Gene via Transposon Tagging

Another approach for locating and isolating the A and N genes is through the use of transposable element systems. Generically called "jumping genes", these automonous elements jump from chromosome to chromosome altering the genetic structure of the genome and creating mutations. One transposable element termed mutator "Mu" is particularly active and has been used successfully to locate the position of genes as well as providing a marker for their isolation (Chomet, 1994; Walbot et al., 1986). When Mu enters a particular site or gene on a chromosome it modifies the sequence of that gene, thereby altering its expression. As one example in maize, insertion of Mu element into the Wx (non-waxy) locus alters the gene so as to produce a wx (waxy) phenotype which expresses itself by modifying the structure of the starch granules in the seed. When this occurs, Mu leaves a particular genetic fingerprint at that locus; thereby enabling isolation of the corresponding region and gene by established methods (Chandler et al., 1994; Martienssen et al., 1989; and O'Reilly et al., 1985).

We have successfully transmitted the Mu element into a 30Mz+9Tr chromosome line by simple backcrossing and generation of 40Mz+9Tr $B_{III}$ hybrid individual via a 2n+n mating. Increasing these materials will result in a large number of 49 chromosome plants each carrying the Mu element, with the expectation that the Mu element will eventually insert itself into one of the genes controlling apomixis thereby imparting chimeral patterns in the corresponding individuals. To date, high levels of male sterility have been observed to accompany apomictic development in the maize-*Tripsacum* hybrids. Looking for highly male fertile sectors in individual plants will identify that an insertion of the Mu element has occurred at either the A or N loci. In addition, any seed produced on that chimeral sector will be sexually derived. Seed derived on the sector not affected by a Mu insertion will be apomictically derived. Once such events occur, the gene can be isolated and cloned via the 220 bp terminal inverted repeat "flag" used by geneticists to identify a Mu insertion. When a mutant for the apomixis gene of interest is found, the first step in locating the gene would be to probe a Southern blot containing DNA from the mutated stock with a publicly available Mu1 probe. Outcrossing and segregation of the mutated locus and its association with the Mu1 probe unquestionably identifies the linkage of the probe, the Mu insertion, to the gene of interest.

Other transposable element systems that could be used for locating and isolating the A and N genes include the Ac/Ds system (Shure et al., 1983; Federoff et al., 1983; and Dellaporta et al., 1994) and the Spm system (Cone, 1994).

TRANSFORMING PLANTS WITH GENES FOR APOMIXIS

Once the genes associated with apomixis are isolated, they can be inserted into plasmids for increase, maintenance and amplification by known procedures. Several methods are presently known for insertion of genes into plant and animal material. These range from pollen transformation techniques (Ohta, Y. 1986; Smith et al., 1994; deWet et al., 1985, all herein incorporated by reference), electroporation techniques (Rhodes et al., 1988; Krzyzk et al., 1995; both herein incorporated by reference), and microprojectile gene transfer techniques. Some methods utilize polyethylene glycol mediated systems to assimilate the provided gene into a cell line. Basically, each method is designed for implanting selected genes into plants cells (or protoplasts) and incorporating those genes into the genome of the selected species (Kamo et al., 1987). Insofar as apomictic reproduction may be under the control of either expressed or repressed proteins as yet to be determined, it may be necessary to introduce appropriate regulatory sequences for appropriate control of expression in the host plant.

The microprojectile-mediated gene transfer technique is probably considered the most reliable and effective method utilized technique in the industry today. Essentially, multiple copies of the gene to be inserted is placed on any of a variety of projectile mediums (silicon carbide fibers, tungsten particles, gold particles, etc.) and inserted into a so-called gene gun. Typically by an infusion of air or pressure system, the particles are projected into a callus of plant tissue. Specific systems for identifying the incorporation of the gene into a callus (also called reporter genes) are the *E. Coli* vidA "GUS" gene and the anthocyanin regulatory genes C1 and B. Once transformed cells are identified, they are removed from the callus and transferred to an appropriate growth media. Eventually through standard tissue culture processes of callus transfer from growth to regeneration media, intact plants are generated. Field studies and progeny testing confirm stable expression of apomictic reproduction and thus incorporation of the appropriate alleles into the genome. Successful transformation of maize by this method is reported by Lowe et al. (1995), herein incorporated by reference.

Of course other transformation methods could be used as well, such as infection with Maize Streak Virus (MSV) or with *Olpidium* zoospores vectoring a reassembled nucleoprotein complex incorporating the genes for apomixis (Langenberg et al., 1995).

Nonlimiting categories of plants that can be used to receive the apomictic gene(s) are those of agronomic and horticultural importance such as grain crops, forage crops, seed propagated fruits, seed propagated ornamentals, and industrial species. Examples of these, without limitation, are corn, wheat, barley, sorghum, rye, oats, rice, beans, peas, peanuts, lentils, tomatoes, peppers, watermelons, apples, oranges, grapefruit, lemons, limes, pearl millet, alfalfa, onions, peppers, beets, sugar beets, turnips, broccoli, cabbage, potatoes, soybeans, sunflower, flax, mustard, safflower, rape, cotton, tobacco, etc.

EXPRESSION OF APOMICTIC GENE PRODUCTS

As alluded to above, apomictic reproduction may be under the control of either expressed or repressed proteins. For detecting and identifying these proteins, the protein profile of a non-transformed cell line could be compared with that of a similar transformed cell line. For instance, if the genes for apomixis were implanted into the maize inbred Mo17, its protein profile could be compared to that of the standard Mo17 maize inbred by methods as well known in the art thereby revealing proteins instrumental in apomictic reproduction. Isolation, elution and biochemical analysis could be conducted by conventional means.

UTILITY OF APOMICTS

The present invention is particularly useful for producing true-breeding hybrids thereby simplifying the production of commercial $F_1$ seed. The occurrence of apomictic reproduction in commercial, cultivated crop plants would eliminate many of the drawbacks of conventional hybrid production, including 1) inhibiting self pollination; 2) increasing and maintaining large quantities of male sterile, maintainer and restorer lines; and 3) planting large acreages of both male and female parents of a hybrid to produce the commercial hybrid when hybrid seed is harvested only from the female parent.

Apomixis increases the opportunity for producing superior gene combinations. An obligate apomictic genotype, regardless of genetic heterozygosity, chromosome number or chromosome constitution (i.e., interspecific crosses) breeds true. Apomixis broadens the gene pool and lessens the genetic vulnerability of commercial hybrids because it does not require females with the male sterility inducing system to produce commercial hybrids.

The apomictic crop plants contemplated herein can be used as forage or grain cultivars or used as male pollinators on sexual germplasm to produce new apomictic forage and grain hybrids. The apomictic plants can also be used as a source of the gene(s) controlling apomixis as described above. The seed of these plants is of course useful for food, feed, and propagative material. The seed is also useful as as source of starch, protein, oil and other constituents which can be isolated or otherwise processed by methods which are well known in the art.

It is understood that reference herein to apomictic plants, either generally or specifically, is intended to encompass all vegetative and propagative forms of such plants, to include the growing or harvested plant, seed, pollen, roots, stems, leaves and other various plant parts and seed components, especially those which can be used for generating progeny of the plants, whether by conventional or tissue culture techniques.

EXAMPLE 1

The apomictic materials of this invention were derived from an F1 hybrid individual hereafter referred to as H278 (20Mz+36Tr). H278 resulted from a cross between a tetraploid maize tester referred to as V182 (2n=2x=40) and a tetraploid (2n=4x=72) Tripsacum dactyloides accession originally obtained from central Mexico and maintained at the Tashkent Botanical Gardens, Tashkent, Uzbikitan (Petrov, et al., 1984b). The V182 tetraploid maize tester is characterized by white seed, colorless pericarp and white cob. The anthers in the tassel are yellow. The genetic symbols for these traits are y (white) vs Y for yellow seeds; P-WW for pericarp-colorless, white cob. Colorless or yellow anthers are designated pl. A diploid maize tester (2n=2x= 20), V174, with anthocyanin pigments was used in subsequent crosses described, below. The V174 plant is purple (anthocyanin pigment) and has colored seed, a colored cob, and a tassel with purple anthers. The genetic symbols for these traits are A, C, Bz1, Bz2, R (colored seed), B (purple plant color), P1 (purple anthers, as opposed to colorless or yellow), and P-WR (colorless pericarp on a red cob). The *T. dactyloides* parent (Tp 209), the maize testers, and the apomictic seed and germplasm derived from H278, are maintained at the Southern Plains Range Research Station, Woodward, Okla.

From the initial F1 hybrid (H278), several genetically identical 56 chromosome (20 maize+36 Tripsacum chromosome) F1 hybrids were generated via apomictic development. A later subsequent backcross of one of the hybrids utilizing a local open-pollinated, diploid maize cultivar (Petrov, et al., 1984b) generated five individuals with 38 chromosomes (20 maize+18 Tripsacum). Of these, 3 individuals were observed to generate progeny which were derived by meiotic or sexual reproductive behaviors. The fourth individual was completely sterile while a fifth individual (H781) produced progeny with a chromosome count of 38. Following more than 15 generations of continuous backcrossing with both diploid (2n=2x=20) and tetraploid (2n=4x=40) maize testers, a large number of individuals and families carrying 18 Tripsacum and 10–40 maize chromosomes were eventually generated from this single individual (H781). Additional studies of these materials generated from H278 and H781 has confirmed their ability to reproduce by apomixis (Kindiger et al., 1995a; Kindiger et al., 1995b).

Following additional backcrosses of the 38 chromosome material with both diploid and tetraploid maize testers, a new set of potentially apomictic materials with 30 maize and 9 Tripsacum chromosomes were generated. These materials were developed by backcrossing an apomictic, 38 chromosome individual with a tetraploid maize tester and screening for a 58 chromosome $B_{III}$-derived hybrid. This individual is the product of a genome accumulation event whereby an unreduced egg does not develop apomictically, but remains receptive to fertilization by a sperm nuclei to form a $B_{III}$ hybrid (a 2n+n mating). The identified 58 chromosome hybrid was again backcrossed by a diploid maize tester. This cross generated an individual with 30 maize+9 Tripsacum chromosomes (See left-most branch of pedigree tree in FIG. 1). Seven such individuals are reported in Table II, below. The reduction from 18 Tripsacum to 9 Tripsacum chromosomes is a result of a sexual process (meiosis I & II), whereby accumulating maize genomes results in a breakdown of apomictic expression. Therefore, the 58-chromosome hybrids (40Mz+18Tr) developed a reduced egg with 20Mz+9Tr chromosomes. This haploid egg was then fertilized by a haploid sperm nuclei (n=10) from the diploid pollen parent, generating an individual with 30Mz+ 9Tr chromosomes.

The family V162 typifies the 30Mz+9Tr hybrids obtained by the aforementioned method. The average of plant measurements taken on 50 individuals of the V162 family yield the following set of morphological characteristics:

Length of ear node leaf—76.22 cm

Plant height (to tassel tip)—173.96 cm

Ear height (to base of top ear)—94.68 cm

Number of tillers—8.5

Width of ear node leaf—5.81 cm

Length of top ear internode—14.12 cm

Number of leaves above top ear—2.12

Number of tassel branches—9.36

Tassel length—29.58 cm

Length of ear—10.65 cm

Number of rows of seed on each ear—4, 2 sets of paired rows

"Male sterile"

A sample comprising at least 2500 seeds obtained from individuals in the V162 family was deposited with the American Type Culture Collection and has been assigned Accession Number ATCC 97233 as previously noted.

TABLE II

Chromosome Counts of Progeny Derived from Various Apomictic 39-Chromosome (30 Mz + 9 Tr) Maize-Tripsacum Hybrids.[1]

| ID (Family-Individual) | 39-chromosome Apomicts | Products from 2n + n matings | Total | % $B_{III}$-derived Hybrids |
|---|---|---|---|---|
| V141-1 | 12 | 0 | 12 | 0 |
| V144-6 | 15 | 0 | 15 | 0 |
| V162-2 | 18 | 2 | 20 | 10 |
| V162-6 | 11 | 0 | 11 | 0 |
| V162-7 | 10 | 0 | 10 | 0 |
| V162-8 | 35 | 2 | 37 | 5.4 |
| V164-3 | 17 | 1 | 18 | 5.5 |

[1] Mz and Tr refer to maize and Tripsacum chromosomes, respectively.

EXAMPLE 2

In excess of 40 hybrid families possessing 30, 40 or 50 maize and 9 Tripsacum chromosomes were produced as described in Example i and evaluated by a plurality of techniques for some of the apomictic reproductive behaviors and characteristics previously described. Materials evaluated for the winter nursery were grown in the greenhouse from February to April. The greenhouse was maintained at 25 C. (+/- 5 C.) and a 9 h day length was provided by 1000 W metal halide lamps.

I. Occurrence of Apomictic Progeny

Chromosome counts were performed by the method of Kindiger (1993, herein incorporated by reference). Chromosome counts of each family identify that all individuals possessed a chromosome count consisting of 39 chromosomes. A careful karyotype of these individuals, based on the known karyotypes of maize and Tripsacum, indicate that each of these individuals possesses 30 maize chromosomes and 9 of the smallest Tripsacum chromosomes (i.e. the 9B set). In comparison to a maize karyotype, the largest Tripsacum chromosome (of the 9B set) is smaller than chromosome 6, 7, and 8 of maize. In addition, due to difference in size, arm ratios, and knob constitution, none of the 9 Tripsacum chromosome resemble any chromosomes of the maize complement, with the possible exception of chromosome 10 of maize. Each of the 9 *Tripsacum* chromosomes has a very small short arm and *Tripsacum* Chromosome No. 16, which carries the nucleolar organizing region (satellite region) in the *Tripsacum* genomic complement, is represented.

Individuals from each family were analyzed for potential 'off-types' utilizing the established isozyme systems for Adh, Acp, Mdh, Phi, Pgd, and Pgm. Electrophoretic techniques for each isozyme system, as described by Stuber et al., (1988) were used for the analysis. The analysis indicated no isoenzymatic variability within and among the materials investigated.

II. Occurrence of $B_{III}$ Derived Hybrids

As previously discussed, it was expected that the occurrence of $B_{III}$ hybrids would be exhibited in the maize-*Tripsacum* hybrids if the apomictic *Tripsacum* genes were fully functional in a maize background.

The frequency of observed $B_{III}$ derived hybrids obtained from several maize-*Tripsacum* backcross hybrids, based on chromosome counts, can be extracted from Table II, above. The frequency of 2n+n matings ($B_{III}$ hybrids) in family V162 is 4/78 or 5.1%. For family V164, the frequency is 1/18 or 5.6%. It is apparent from Table III, below, that similar individuals generated from 2n+n matings are observed in apomictic families of *T. dactyloides*, but at greater frequency. The comparison of $B_{III}$ hybrids generated from 2n+n matings further indicate that the apomictic genes of *Tripsacum* are present and functional in the 39 chromosome hybrids. The production of $B_{III}$ hybrids has not been observed in the sexual, diploid forms of *Tripsacum* and would not be expected.

TABLE III

Frequency of $B_{III}$ Derived Hybrids in Selected Apomictic, *T. dactyloides* Accessions*

| ID | Original Parental Ploidy | No. of Progeny Evaluated | No. of $B_{III}$-Derived Hybrids[b] | Percent |
|---|---|---|---|---|
| WW1008 | 2n = 4x = 72 | 107 | 7 | 6.5% |
| WW2190 | 2n = 4x = 72 | 49 | 22 | 44.9% |
| WW1766 | 2n = 3x = 54 | 113 | 28 | 24.8% |
| WW2296 | 2n = 3x = 54 | 111 | 31 | 27.9% |

*Data based on chromosome counts obtained from 4x × 4x, 4x × 2x, 3x × 2x and 3x × 4x matings.
[b]Includes all 2n + n matings which gave either new tetraploids (2n = 4x = 72), pentaploids (2n = 5x = 90) or hexaploid (2n = 6x = 108) progeny.

III. Occurrence of Polyembryony

Evaluations performed on the 30Mz+9Tr apomictic, maize-*Tripsacum* hybrids includes data obtained from 3 apomictic families (106 individuals). Of these, 25 (24%) were polyembryonic. The results of the evaluations are reported in Table IV, below.

TABLE IV

Comparison of Polyembryony Frequency between Apomictic Tripsacum Accessions and Apomictic 30 Mz and 9 Tr Hybrids

| Family/Ploidy | Number of Progeny | Number Polyembryonic | Percent Polyembryony |
|---|---|---|---|
| (Apomictic Tripsacums) | | | |
| WW1008 (4x) | 209 | 39 | 18.7 |
| WW2167 (4x) | 315 | 47 | 14.9 |

TABLE IV-continued

Comparison of Polyembryony Frequency between Apomictic Tripsacum Accessions and Apomictic 30 Mz and 9 Tr Hybrids

| Family/Ploidy | Number of Progeny | Number Polyembryonic | Percent Polyembryony |
|---|---|---|---|
| WW2031 (4x) | 47 | 4 | 8.5 |
| WW2296 (3x) | 237 | 49 | 20.7 |
| WWFT1-12 (3x) | 2355 | 611 | 25.9 |
| (Apomictic 39 chromosome maize-Tripsacum Hybrids) | | | |
| V162-8 | 37 | 10 | 27.0 |
| V162-2 | 20 | 5 | 25.0 |
| V141-1 | 12 | 2 | 16.6 |
| V137 | 37 | 8 | 21.6 |

IV. Effect of Ploidy on Apomictic Expression

Seed set on maize/*Tripsacum* hybrid individuals possessing 48, 58, 68, 78 and 88 chromosomes (40, 50, 60, 70 maize+18 *Tripsacum* chromosomes) respectively, indicate a substantial loss in seed setting capacity above the 58 chromosome level (Table V). Observations on seed set of pentaploid (5x=5n=90) and hexaploid (6x=6n=108) *Tripsacum* individuals generated from apomictic tetraploids also indicate a dramatic reduction in seed set (0–1% fertility) following an increase in ploidy by the identical genome accumulation mechanism (i.e. 2n+n matings).

TABLE V

Maternal Fertility Among Various Apomictic Maize-Tripsacum Hybrids

| Chromosome Constitution[1] | Number of Families Evaluated | Percent Fertility[2] |
|---|---|---|
| 20 Mz + 18 Tr | 6 | 30.0 |
| 30 Mz + 18 Tr | 6 | 15.0 |
| 40 Mz + 18 Tr | 4 | 5.0 |
| 50 Mz + 18 Tr | 2 | 0 |
| 60 Mz + 18 Tr | 1 | 0 |
| 70 Mz + 18 Tr | 2 | 0 |

[1]Mz and Tr refer to the number of maize and Tripsacum chromosomes, respectively.
[2]Is a bulk value based on families possessing identical chromosome constitutions. The value is an average estimate related to an approximate number of potential seed which could be set on infloresence.

V. RAPD Analysis

RAPD analysis, were performed on DNA extracted from fresh, lyophilized leaf material to determine genetic uniformity or identify variation among the 19 individuals evaluated. DNA extractions were performed following the method of Saghai-Maroof et al., (1984). Individuals were assayed by RAPD techniques following the protocol developed by Williams et al., (1990). Reactions were carried out on approximately 5 ng of plant DNA. Taq polymerase and 10X reaction buffer were purchased from Perkin Elmer (Branchburg, N.J.). The 40 primers utilized in the RAPD study were decamer oligonucleotides available as Kits A thru K, purchased from Operon Technologies (Alameda, Calif.). PCR amplifications were carried out in a M.J. Research, PTC-100 Thermocycler with a "hot-lid" accessory. The PCR amplification reaction was programmed for 1 cycle of 94° C. for 1.5 minutes followed by 34 cycles of 94° C. for 1 minute; 45° C. for 2 minutes and 72° C. for 2 minutes and then 1 final cycle of 45° C. for 2 minutes and 72° C. for 5 minutes. Following amplification, RAPD products were held at 4° C. until they were separated on a 1.5% agarose gel in 1X TBE buffer at 100 V for 4 hours. Visualization was achieved under UV light following staining in ethidium bromide for 1 hour. Due to the occasional formation or presence of artifactual RAPD bands, faint or inconsistent bands were disregarded. Only bright bands were considered during the evaluations. In addition, replicate runs were carried out on individuals or families which exhibited questionable or variant profiles to verify their authenticity/reproducibility.

A set of 8 maize checks, originally used in the Russian maize-*Tripsacum* program were also included to help identify the relative informativeness of the primers in a maize background. Previous evaluations on the relative informativeness of these decamer primers indicate that they are able to detect genetic variability among apomictic and non-apomictic offspring. None of the RAPD evaluations identified variation between the families or individuals evaluated, other than that observed in the occasional $B_{III}$-derived hybrid.

RAPD markers which were identified as being associated with apomictic reproduction (i.e. the long arm of Tr16) are reported in Table VI, below. The assignment of these seven markers to the Tripsacum chromosome carrying the genes for apomixis are 100% valid across lines of descent. That is, regardless of whether the analyzed individual was derived from a parent with 18 or 9 *Tripsacum* chromosomes, or was derived from a different line of descent, the markers are 100% accurate in their association to apomictic reproduction.

Blakey (1993), herein incorporated by reference, describes two RFLP markers, UMC62 and UMC134, associated with linkage group L of Tripsacum. Due to the generation of the Mz6L-Tr16L translocation, we now know that linkage group L represents the long arm of *Tripsacum* chromosome 16. Therefore, by inference, markers UMC62 and UMC134 must be associated with apomixis. In addition, Leblanc et al., (1995) have reported three maize RFLP markers which are also located on the distal tip of Mz6L (UMC62, UMC28 and CSU68). These markers can also be used to follow apomixis in a breeding program.

TABLE VI

Primers and Corresponding RAPD Markers Associated with Apomixis

| Primer | Approx. MW Marker | SEQ ID NO. | Primer Sequence |
| --- | --- | --- | --- |
| OPA-01 | 391 | 1 | CAGGCCCTTC |
| OPA-06 | 251 | 2 | GGTCCCTGAC |
| OPA-12 | 152 | 3 | TCGGCGATAG |
| OPG-06 | 552 | 4 | GTGCCTAACC |
| OPI-11 | 419 | 5 | ACATGCCGTC |
| OPJ-14 | 1200 | 6 | CACCCGGATC |
| OPK-06 | 489 | 7 | CACCTTTCCC |

The general relationship among five families used to develop the RAPD markers associated with apomixis is depicted in FIG. 1. There are five distinct lines of descent. Four of the five families were derived by entirely differing pathways as noted by the chromosome numbers. V58A is distinct from all other families in that it is phenotypically more maize-like than the other families, having more rows per ear and few to no tillers. The bottom row of the chart represents sexually derived individuals which have lost their apomictic reproductive potential with the exception of V9 (FIG. 1, lower right) which carries the Mz6L-Tr16L translocation. The RAPD markers associated with apomixis are absent in these individuals and are present in each of their apomictic parents.

EXAMPLE 3

Figure 2:
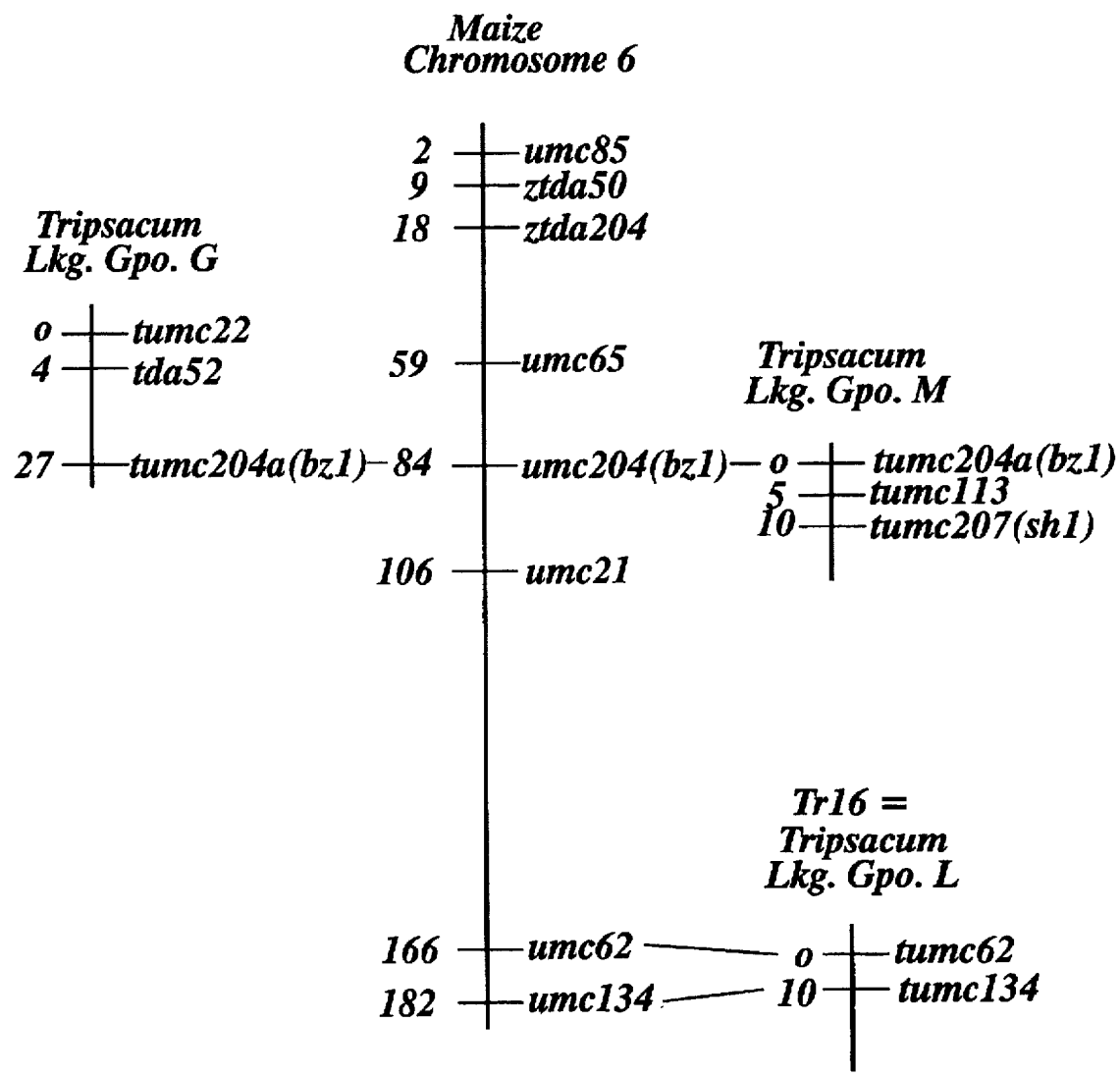
FIG. 2 shows a relative molecular map of maize Chromosome No. 6, including maize and homeologous *Tripsacum* linkage groups.

A 30Mz+9Tr chromosome maize/*Tripsacum* hybrid identified as V9 was derived by the same procedure described in Example 1, except that during an apomictic developmental stage, a meiotic event (synapsis and recombination) occurred between homoeologous regions of Mz6 and Tr16, thereby generating a Mz6L-Tr16L translocation. FIG. 2 is a relative molecular map of Mz6. Relative map units are shown to the left of the vertical lines and specific genes are shown to the right. *Tripsacum* linkage groups G and M are homologous and colinear with regions above and below map position 84, respectively. On the lower right of the map, the Tr16 long arm translocation is depicted as Linkage Group L (Blakey, 1993). The Mz6L-Tr16L translocation stock (V9) appears to have retained most, if not all, of Mz6L and is missing the Tr16S arm. Of 18 RAPD markers which were originally associated with apomictic reproduction based upon screening performed on Tripsacum material, apomictic maize-*Tripsacum* hybrids carrying 36, 18 and 9 *Tripsacum* chromosomes, the sexually derived maize/*Tripsacum* hybrids (i.e. V142-3, missing Tr16 from its genetic complement) and the tetrapolid maize testers, only the seven markers described above in Table VI were present in the Mz6L-Tr16L stock as indicated by the corresponding RAPD bands. Therefore, all 18 RAPD markers are located on Tr16. Of these, seven are located on Tr16L. Thus, Linkage Group L of Mz6L-Tr16L is clearly indicated to carry the genes for apomictic reproduction.

Figure 3A:
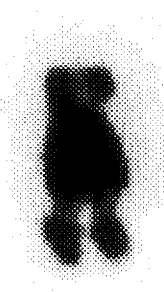
Figure 3B:
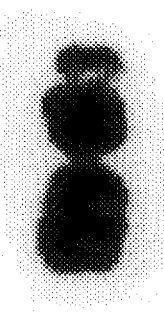
Figure 3C:
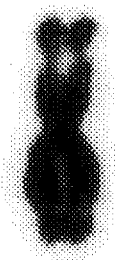

FIGS. 3A, 3B, and 3C present images of chromosomes representing chromosomes Tr16, Mz6 and the Mz6L-Tr16L translocation, respectively. All RAPD markers assigned to a chromosome arm and associated with apomixis are identified by the OP (Operon) designation followed by the specific kit (A-K) and specific primer number (1-20) assigned to each decamer primer by Operon Technologies, Alameda, Calif., USA (i.e. OPA-01). All RFLP markers assigned to Tr16L and Mz6L are identified by the UMC or CSU designation followed by a particular number assigned to the probe by the developer (i.e. UMC134). Line drawings 3A-1, 3B-1, and 3C-1 of chromosomes Tr16, Mz6 and the Mz6L-Tr16L translocation, respectively are provided (complete with satellite) to orientate the viewer to the relative position of the RAPD and the RFLP markers along each chromosome. Satellites are depicted by the large black circles. Centromeres are indicated by the small open circles. The long (L) or short (S) arms of each chromosome are assigned to each line diagram using the prefix Tr and Mz to represent the *Tripsacum* and maize chromosomes (i.e. Tr16L or Tr16S). The Mz6L-Tr16L translocation is identified as "V9: Mz6L-Tr16L" and is illustrated in the bottom line drawing.

EXAMPLE 4

The Mu gene has been inserted into the apomictic materials via the 2n+n reproductive events. Plants having 30Mz+9Tr chromosomes (V162) were crossed by 2n=2x=20 maize plants (obtained from D. Robertson, Iowa State Univ.) carrying several copies of active Mu elements. The diploid maize seed stock carries the gene A C R P1 which gives color to the maize seed for easy identification. Individuals obtained from the cross possessing 40Mz+9Tr chromosomes are products of a 2n+n mating and will carry the Mu element.

It is understood that the foregoing detailed description is given merely byway of illustration and that modifications and variations may be made therein without departing from the spirit and scope of the invention. The scope of the present invention is not limited to the seeds deposited, insofar as the deposit is intended merely as an illustration of a single embodiment of the invention and a source for further improvements thereon within the ordinary skill of a person in the art.

REFERENCES

Asker, S. E. and L. Jerling. (1992). Apomixis in Plants. 1st Edition. CRC Press, Boca Raton, Fla.

Bashaw, E. C. & Hanna, W. W. (1990a). Apomictic reproduction. In: Reproductive Versatility in the Grasses. Ed. by G. P. Chapman. Cambridge Univ. Press, pp. 100–130.

Bashaw, E. C. and K. W. Hignight. (1990b). Gene transfer in apomictic buffelgrass through fertilization of an unreduced egg. Crop Sci. 30:571–575.

Bashaw, E. C., M. A. Hussey & Hignight, K. W. (1992). Hybridization (N+N and 2N+N) of facultative apomictic species in the Pennisetum agamic complex. Int. J. Plant Sci. 153:466–470.

Bergquist, R. R. (1981). Transfer from Tripsacum dactyloides to corn of a major gene locus conditioning resistance to Puccinia sorghi. Phytopathology 71:518–520.

Blakey, (Aug. 1993). Ph.D dissertation: A Molecular Map in Tripsacum dactyloides, Eastern Gamagrass, Publ. No. 9412465, Univ. of Missouri, Columbia.

Brown, W. V. & Emery, W. H. P. (1958). Apomixis in the Gramineae: Panicoideae. Am. J. Bot. 45:253–263.

Burson, B. L., P. W. Voigt, R. A. Sherman and C. L. Dewald. (1990). Apomixis and sexuality in eastern gamagrass. Crop Sci. 30:86–89.

Burson, B. L. (1992). Cytology and reproductive behavior of hybrids between Paspalum urvillei and two hexaploid P. dilatatum biotypes. Genome 35:1002–1006.

Burton, G. W., and Forbes, I. (1960). The genetics and manipulation of obligate apomixis in common bahiagrass (Paspalum notatum Flugge) pp. 66–71. In: Proc. 8th Int. Grassland Congr., Alden Press: Oxford, England.

Chandler, V. (1994). "Overview of cloning genes using transposon tagging." pp. 647–652, In: M. Freeling & V. Walbot (eds.), The Maize Handbook. Springer-Verlag, New York, Inc.

Chomet, P. S. (1994). "Transposon Tagging with Mutator", pp. 243–249, In: M. Freeling & V. Walbot (eds.), The Maize Handbook. Springer-Verlag, New York, Inc.

Cohen, J. I., and Galinat, W. C. (1984). Potential use of alien germplasm for maize improvement. Crop Science 24:1011–1015.

Collins, G. B. (1977). Production and utilization of anther-derived haploids in crop plants. Crop Science 17:583–586.

Cone, K. (1994). Transposon tagging with Spm. pp. 240–242. In: M. Freeling & V. Walbot (eds.), The Maize Handbook. Springer-Verlag, New York, Inc.

Conger, B. V., Novak, F. J., Afza, R. and Erdelsky, K. (1987). Plant Cell Reports 6:345–347.

Conner, H. E. (1979). Breeding systems in the grasses: a survey. New Zealand J. Bot. 17:547–574.

Dellaporta, S. L. and Moreno, M. A. (1994). Gene tagging with Ac/Ds elements in maize. pp. 219–233. In: M. Freeling & V. Walbot (eds.), The Maize Handbook. Springer-Verlag, New York, Inc.

deWet, J. M. J., Engle, L. M., Grant, C. A., and Tanaka, S. T. (1972). Cytology of maize-Tripsacum introgression. Am. J. Bot. 59:1026–1029.

deWet, J. M. J., Harlan, J. R. (1974). Tripsacum-Maize Interaction: A novel cytogenetic system. Genetics 78:493–502.

deWet, J. M. J. (1985) International Patent Application WO 85/01856.

Dujardin, M. and Hanna, W. W. (1983). Apomictic and sexual pearl millet x Pennisetum squamulatum hybrids. J. of Heredity 74:277–279.

Dujardin, M. and Hanna, W. W. (1989). Developing apomictic pearl millet-Characterization of a BC3 plant. J. Genet. Breed. 43:145–151.

Farquharson, L. I. (1955). Apomixis and polyembryony in Tripsacum dactyloides. Am. J. Bot. 42:737–743.

Federoff, N., Mauvais, J. and Chaleff, D. (1983). Molecular studies on mutations at the shrunken locus in maize caused by the controlling element Ds. J. Mol. Appl. Gen. 2:11–29.

Galinat, W. C. (1973). Intergenomic mapping of maize, teosinte, and Tripsacum. Evolution 27:644–655.

Green, C. E. and Philips, R. L. (1975). Plant regeneration from tissue cultures of maize. Crop Science 15:417–421.

Hanna, W. W., J. B. Powell, J. C. Millot & Burton, G. W. (1973). Cytology of obligate sexual plants in Panicum maximum Jacq. and their use in controlled hybrids. Crop Sci. 13:695–697.

Harlan, J. R., Brooks, M. H., Borgaonkar, D. S., and deWet, J. M. J. (1964). Nature and inheritance of apomixis in Bothriochloa and Dichanthium. Bot. Gaz. 125:41–46.

Kamo, K. K., Chang, K. L., Lynn, M. E. and Hodges, T. K., (1987). Embryogenic callus formation from maize protoplasts. Planta 172: 245–251.

Kermicle, J. L. (1969). Androgenesis conditioned by a mutation in maize. Sci. (Washington, D.C.) 166:1422–1424.

Kindiger, B. (1990). Cytological evidence supporting a procedure for directing and enhancing pairing between maize and Tripsacum. Genome 33:495–500.

Kindiger, B. (1993). A technique for the preparation of somatic chromosomes of maize. pp. 481–483. In M. Freeling and V. Walbot (eds.) The Maize Handbook. 1st Edition. Springer-Verlag, New York, Inc.

Kindiger, B. and S. Hamann. (1993). Generation of Haploids in Maize: A modification of the indeterminate gametophyte (ig) system. Crop Sci. 33:342–344.

Kindiger, B. and Dewald, C. (1994a). Genome accumulation in eastern gamagrass, Tripsacum dactyloides (L). L. (Poaceae). Genetica 92:197–201.

Kindiger, B. and Vierling, R. (1994b). Comparative isozyme polymorphisms of North American eastern gamagrass, Tripsacum dactyloides var. dactyloides and maize, Zea mays L. Genetica 94:77–83.

Kindiger, B., Sokolov, V. and Khatypova, I. V. (1995a). Evaluation of Apomictic Reproduction in a set of 38 chromosome maize-Tripsacum backcross hybrids. Crop Science (in press).

Kindiger, B. and Dewald, C. (1995b). System for genetic change in apomictic eastern gamagrass, Tripsacum dactyloides. Crop Science (in press).

Kindiger, B., Sokolov, V. and Dewald, C. (1995c). A comparison of apomictic reproductive behaviors in eastern gamagrass (Tripsacum dactyloides (L.)L.) and maize-Tripsacum hybrids. Genetica (in press).

Koltunow, A.M. (1993). Apomixis: Embryo sacs andDewald, C. (1995b). embryos formed without meiosis or fertilization in ovules. The Plant Cell 5:1425–1437.

Krzyzk, R. A. et al. (1995). U.S. Pat. No. 5,384,253.

Langenberg, W. G. et al., (1995). U.S. Pat. No. 5,416,010.

Leblanc, O., Peel, M. D., Carman, J. G. and Savidan, Y. (1995a). Megasporogenesis and megagametogenesis in several Tripsacum species (Poaceae). Am. J. Bot. 82:57–63.

Leblanc, O., Grimanelli, D., Gonzalez-de-Leon, D., and Savidan, Y. (1995b). Detection of the apomictic mode of reproduction in maize-Tripsacum hybrids using maize RFLP markers. Theoretical & Applied Genetics 90:1198–1203.

Lowe, K., Bowen, B., Hoerster, G., Ross, M., Bond, D., Pierce, D., and Gordon-Kamm, W., (1995). Germline tranformation of maize following manipulation of chimeric shoot meristems. *Bio/Technology* 13:677–682.

Maguire, M. P. (1961). Divergence in *Tripsacum* and *Zea* chromosomes. *Evolution* 15:394–400.

Maguire, M. P. (1962). Chromatid interchange in allodiploid maize-*Tripsacum* hybrids. *Can. J. Genet. Cytol.* 5:414–420.

Mangelsdorf, P. C., and Reeves, R. G. (1931). Hybridization of maize, *Tripsacum* and Euchlaena. *J. Hered.* 22:329–343.

Mangelsdorf, P. C., and Reeves, R. G. (1939). The origin of Indian corn and its relatives. Texas Agric. Exp. Stn. Bull. No. 574.

Martiennsen, R. A., Barken, A., Freeling, M. and Taylor, W. C. (1989). Molecular cloning of a maize gene involved in photosynthetic membrane organization that is regulated by Robertson's Mutator. *EMBO J.* 8:1633–1639.

Maxon, E. J., Maxon, N. P., (1989), WO 89/00810.

Morrison, R. A. and Evans, D. A., (1988). Haploid plants form tissue culture: New plant varieties in a shortened time frame. *Bio/Technology* 6:684–690.

Ohta, Y. (1986). High-efficiency genetic transformation of maize by a mixture of pollen and exogenous DNA. *Proc. Natl. Acad. Sci. U.S.A.* 83:715–719.

O'Reilly, C., Shepherd, N. S., Pereira, A., Schwarz-Sommer, Z., Betram, I., Robertson, D. S. and Peterson, P. A. (1985). Molecular cloning of the al locus of *Zea mays* using the transposable elements En and Mul. *EMBO J.* 4:877–882.

Pescitelli, S. M. and Petolino, J. F. (1988). Microspore development in cultured maize anthers. *Plant Cell Reports* 7:441–444.

Petrov, D. F., (1957). Znachenie apomiksisa alya azkrepleniya geterozisa (Significance of apomixis for fixing heterosis). *Dokl. Akad. Nauk. SSSR*, 112:954–957.

Petrov, D. F., N. I. Beloussva, E. S. Fokina & Sorokina, T. P. (1978). The engaging of chromosome parts of *Tripsacum* in the chromosome of maize as related to transmission transferring of apomixis elements. 14th International Congress of Genetics, Moscow, pp46–75.

Petrov, D. F., N. I. Belousova and Fokina, E. S. (1979). Inheritance of apomixis and its elements in corn-*Tripsacum* hybrids. Genetika 15:1827–1836.

Petrov, D. F., N. I. Belousova and Fokina, E. S. (1984a). In: Problems of apomixis and remote hybridization. Novosibirsk, Nauka, pp. 29–41.

Petrov, D. F., N. I. Belousova, E. S. Fokina, L. I. Laikova, R. M. Yatsenko and Sorokina, T. P. (1984b). Transfer of some elements of apomixis from *Tripsacum* to maize. In D. F. Petrov (ed.) Apomixis and Its Role in Evolution and Breeding. Oxonian Press Ltd., New Delhi, pp. 9–73.

Reeves, R. G., and Bockholt, A. J. (1964). Modification and improvement of a maize inbred by crossing it with *Tripsacum*. *Crop Sci.* 4:7–10.

Rhodes, C. A. et al. (1988). Genetically transformed maize plants from protoplasts. *Science* 240:204–207

Rieger, R., A. Michaelis and Green, M. M. (1976). In Glossary of Genetcs and Cytogenetics. Springer-Verlag, New York, N.Y.

Saghai-Maroof, M. A., K. M. Soliman, R. A. Jorgensen and R. W. Allard. (1984). Ribosomal DNA spacer-length polymorphisms in barley: Mendelian inheritance, chromosomal location and population dynamics. *PNAS* (USA) 81:8014–8018.

Sherman, R. A., P. W. Voigt, B. L. Burson & Dewald, C. L. (1991). Apomixis in diploid x triploid *Tripsacum dactyloides* hybrids. Genome 34:528–532.

Simone, G. W., and Hooker, A. L. (1976). Monogenic resistance in corn to *Helminthosporium turcicum* derived from *Tripsacum floridanum*. Proc. Am. Phytopathol. Soc. 3:307.

Smith et al. (1994). Expression of GUS and CAT activities using electrotransformed pollen. *Plant Science* 104:49–58.

Stuber, C. W., J. F. Wendel, M. M. Goodman and Smith J. S. C. (1988). Techniques and scoring procedures for starch gel electrophoresis of enzymes from maize (*Zea mays* L.). Technical Bull. 286, North Carolina Agric. Res. Serv., North Carolina State University, Raleigh, N.C.

Shure, M., Wessler, S. and Federoff, N. (1983). Molecular identification and isolation of the Waxy locus in maize. *Cell* 35:225–233.

Ting, Y. C., (1985). Meiosis and fertility of anther cultured derived maize plants. *Maydica* 30:161–169.

Walbot et al., (1986). "Properties of Mutable Alleles Recovered from Mutator Stocks of *Zea mays* L. pp. 115–142, In: Gustafson et al. (eds), Genetics, Development and Evolution, Plenum Press, New York.

Williams, J. G. K., Kubelik, A. R., Livbak, K. J., Rafalski, J. A. and Tingey, S. V. (1990). DNA polymorphisms amplified by arbitrary primers are useful as genetic markers. *Nucleic Acids Res.* 18:6531–6535.

Wilson, K. J. and R. A. Jefferson. (1992). Preface. In K. J. Wilson (ed.) Proceedings of the International Workshop on Apomixis in Rice, Changsha, People's Republic of China. 13 Jan.–15 Jan. 1992. Hunan Hybrid Rice Research Center, Changsha, People's Republic of China.

Yudin, B. F. and Sokolov, V. A. (1989). Towards regular apomixis in maize, achieved by experiment. *Genetic Manipulation in Plants* 5:36–40.

---

We claim:

1. Apomictic maize having at least one dominant gene N for controlling nonreduction of the egg and at least one dominant gene A for controlling apomictic development of the egg.

2. The apomictic maize of claim 1, wherein the genome has exactly one dominant gene A and at exactly one dominant gene N.

3. The apomictic maize of claim 1 having a karyotype comprising the long arm of *Tripsacum dactyloides* chromosome number 16 carrying the alleles for apomixis.

4. The apomictic maize of claim 1 characterized by a Mz6-Tr16 translocation.

5. An apomictic maize/*Tripsacum* hybrid having a karyotype wherein the ratio of maize chromosomes: *Tripsacum* chromosomes is at least 30:9, and wherein said hybrid has at least one dominant gene N for controlling nonreduction of the egg and at least one dominant gene A for controlling apomictic development of the egg.

6. The hybrid of claim 5, wherein the karyotype comprises from 30–70 chromosomes of maize and 9 chromosomes of *Tripsacum*.

7. The maize of claim 1 having at least one marker on a chromosome carrying a gene for apomixis, which marker is amplified in a polymerase chain reaction by a primer, wherein said primer is selected from the group consisting of SEQ ID NO. 1, SEQ ID NO. 2, SEQ ID NO. 3, SEQ ID NO. 4, SEQ ID NO. 5, SEQ ID NO. 6, and SEQ ID NO 7.

8. Seed of the maize of claim 1.
9. Seed of the maize of claim 2.
10. Seed of the maize of claim 3.
11. Seed of the maize of claim 4.
12. Seed of the hybrid of claim 5.
13. Seed of the hybrid of claim 6.

14. A method of increasing the complement of maize chromosomes in a maize/*Tripsacum* hybrid comprising backcrossing the hybrid with a sexually reproducing maize line and selecting for a $B_{III}$-derived hybrid, wherein said maize/*Tripsacum* hybrid has a ratio of maize chromosomes: *Tripsacum* chromosomes of at least 30:9.

15. The method of claim 14 wherein said maize/*Tripsacum* hybrid comprises 30 chromosomes of *Zea mays* and 9 chromosomes of *Tripsacum dactyloides*.

16. The method of claim 15 wherein said maize/*Tripsacum* hybrid is ATCC Accession No. 97233.

17. The method of claim 15 wherein said maize/*Tripsacum* hybrid comprises a Mz6-Tr16 translocation.

18. A method of increasing the complement of maize chromosomes in a maize/*Tripsacum* hybrid comprising backcrossing the hybrid with a sexually reproducing maize line, selecting for an individual having a Mz6-Tr16 translocation, backcrossing that individual with a sexually reproducing maize line and selecting for a $B_{III}$-derived hybrid.

19. The method of claim 18 wherein said maize/*Tripsacum* hybrid comprises 30 chromosomes of *Zea mays* and 9 chromosomes of *Tripsacum dactyloides*.

20. The method of claim 19 wherein said maize/*Tripsacum* hybrid is ATCC Accession No. 97233.

21. A method of introgressing apomixis into a maize that reproduces sexually comprising transferring into said maize both the dominant allele N responsible for non-reduction and the dominant allele A responsible for apomictic development of an unreduced egg.

22. An isolated region of the long arm of *Tripsacum dactyloides* chromosome 14 comprising the dominant allele N responsible for non-reduction and the dominant allele A responsible for apomictic development of an unreduced egg.

23. The apomictic maize of claim 1, wherein said N and A genes are associated with the Mz6-chromosome.

24. Seed of the maize of claim 23.

25. The apomictic maize/*Tripsacum* hybrid of claim 5 characterized by a Mz6-Tr16 translocation.

26. The apomictic maize/*Tripsacum* hybrid of claim 5, wherein said N and A genes are on a maize chromosome.

27. Seed of the hybrid of claim 25.
28. Seed of the hybrid of claim 26.

* * * * *